US008821409B2

(12) United States Patent
Ku et al.

(10) Patent No.: US 8,821,409 B2
(45) Date of Patent: Sep. 2, 2014

(54) LUNG AEROSOL COLLECTION DEVICE

(75) Inventors: David N. Ku, Decatur, GA (US); Larry J. Anderson, Atlanta, GA (US); Prem A. Midha, Rolla, MO (US); Harris L. Bergman, Atlanta, GA (US); Tamera Scholz, Atlanta, GA (US)

(73) Assignees: The United States of America as Represented by the Secretary of the Department of Health and Human Services, Centers for Disease Control and Prevention, Washington, DC (US); Georgia Tech Research Corporation, Atlanta, GA (US)

( * ) Notice: Subject to any disclaimer, the term of this patent is extended or adjusted under 35 U.S.C. 154(b) by 293 days.

(21) Appl. No.: 13/141,908

(22) PCT Filed: Dec. 21, 2009

(86) PCT No.: PCT/US2009/068961
§ 371 (c)(1),
(2), (4) Date: Sep. 13, 2011

(87) PCT Pub. No.: WO2010/075265
PCT Pub. Date: Jul. 1, 2010

(65) Prior Publication Data
US 2012/0004571 A1      Jan. 5, 2012

Related U.S. Application Data

(60) Provisional application No. 61/140,292, filed on Dec. 23, 2008.

(51) Int. Cl.
*A61B 5/08* (2006.01)
*B65D 81/00* (2006.01)
*A61B 10/00* (2006.01)
*G01N 33/497* (2006.01)
*A61B 5/097* (2006.01)

(52) U.S. Cl.
CPC ......... *A61B 5/097* (2013.01); *A61B 2010/0087* (2013.01); *G01N 33/497* (2013.01); *A61B 5/082* (2013.01)
USPC ............ 600/562; 600/529; 600/532; 600/543

(58) Field of Classification Search
USPC .................................. 600/562, 529, 543, 532
See application file for complete search history.

(56) References Cited

U.S. PATENT DOCUMENTS 3,858,573 A * 1/1975 Ryan et al. .................... 600/543
3,880,591 A * 4/1975 Burroughs .................... 600/529
(Continued)

FOREIGN PATENT DOCUMENTS

DE          19619763        11/1997
WO       2012068374 A3       5/2012

OTHER PUBLICATIONS

International Search Report for International Application No. PCT/US2009/068961, mailed Aug. 25, 2010.
(Continued)

*Primary Examiner* — Rene Towa
*Assistant Examiner* — May Abouelela
(74) *Attorney, Agent, or Firm* — Meunier Carlin & Curfman, LLC (57) ABSTRACT

A device for collecting material from lung aerosols. The device functions by collecting aerosols from the lower airway separated from material in the by collecting air from the upper airway in a chamber that when full causes the remaining exhaled aerosols from the lungs to be captured by a filter. The filter collects sample of material from the separated lung aerosols.

14 Claims, 3 Drawing Sheets

(56) References Cited

U.S. PATENT DOCUMENTS

| | | | | |
|---|---|---|---|---|
| 3,888,630 A * | 6/1975 | Hoeg | ............................ | 436/132 |
| 4,117,714 A * | 10/1978 | Goodson et al. | ............. | 73/31.03 |
| 4,370,986 A * | 2/1983 | Gebhart et al. | ............... | 600/529 |
| 4,517,987 A * | 5/1985 | Sackner et al. | ............... | 600/532 |
| 4,564,021 A * | 1/1986 | Siegmann et al. | ............ | 600/529 |
| 4,900,514 A * | 2/1990 | Fuller | ............................ | 600/397 |
| 5,081,871 A * | 1/1992 | Glaser | ......................... | 73/863.23 |
| 5,465,728 A * | 11/1995 | Phillips | ........................... | 600/543 |
| 5,787,885 A * | 8/1998 | Lemelson | ..................... | 600/309 |
| 5,855,652 A * | 1/1999 | Talley | .............................. | 96/44 |
| 6,017,767 A | 1/2000 | Chandler | | |
| 6,033,368 A * | 3/2000 | Gaston et al. | .................. | 600/532 |
| 6,067,983 A * | 5/2000 | Stenzler | .................... | 128/204.23 |
| 6,158,676 A * | 12/2000 | Hughes | .......................... | 239/405 |
| 6,306,099 B1 * | 10/2001 | Morris | ........................... | 600/529 |
| 6,419,634 B1 * | 7/2002 | Gaston et al. | .................. | 600/532 |
| 6,548,309 B1 | 4/2003 | Moore et al. | | |
| 6,582,376 B2 * | 6/2003 | Baghdassarian | .............. | 600/543 |
| 6,708,688 B1 * | 3/2004 | Rubin et al. | .............. | 128/200.23 |
| 6,726,637 B2 * | 4/2004 | Phillips | ........................... | 600/543 |
| 6,727,073 B1 | 4/2004 | Moore et al. | | |
| 6,824,997 B1 | 11/2004 | Moore et al. | | |
| 6,955,650 B2 * | 10/2005 | Mault et al. | ..................... | 600/531 |
| 7,118,537 B2 * | 10/2006 | Baddour | ........................ | 600/543 |
| 7,364,553 B2 * | 4/2008 | Paz et al. | ......................... | 600/543 |
| 7,425,302 B2 | 9/2008 | Piasio et al. | | |
| 7,547,285 B2 * | 6/2009 | Kline | ............................ | 600/532 |
| 7,718,375 B2 | 5/2010 | Piasio et al. | | |
| 7,988,641 B2 * | 8/2011 | McCawley et al. | ............ | 600/532 |
| 8,002,712 B2 * | 8/2011 | Meka et al. | .................... | 600/543 |
| 8,052,933 B2 * | 11/2011 | Schirmer et al. | ............... | 422/507 |
| 8,627,821 B2 * | 1/2014 | Edwards et al. | .......... | 128/205.22 |
| 2003/0208132 A1 * | 11/2003 | Baddour | ........................ | 600/532 |
| 2004/0161804 A1 * | 8/2004 | McCash et al. | ................. | 435/7.2 |
| 2004/0162500 A1 * | 8/2004 | Kline | ............................ | 600/532 |
| 2005/0065446 A1 * | 3/2005 | Talton | ............................ | 600/529 |
| 2005/0137491 A1 * | 6/2005 | Paz et al. | ......................... | 600/543 |
| 2005/0150385 A1 | 7/2005 | Huang et al. | | |
| 2007/0100250 A1 * | 5/2007 | Kline | ............................ | 600/532 |
| 2007/0123792 A1 * | 5/2007 | Kline | ............................ | 600/538 |
| 2007/0203424 A1 * | 8/2007 | Kline | ............................ | 600/543 |
| 2008/0045825 A1 | 2/2008 | Melker et al. | | |
| 2008/0053434 A1 | 3/2008 | Wightman et al. | | |
| 2008/0053456 A1 * | 3/2008 | Brown et al. | ............ | 128/207.16 |
| 2008/0096728 A1 * | 4/2008 | Foley et al. | ...................... | 482/13 |
| 2008/0221471 A1 * | 9/2008 | Djupesland et al. | ........... | 600/543 |
| 2008/0254471 A1 * | 10/2008 | Bordano | ........................... | 435/6 |
| 2009/0024058 A1 * | 1/2009 | Blowick et al. | ................ | 600/582 |
| 2009/0038416 A1 | 2/2009 | Bonner | | |
| 2009/0187113 A1 * | 7/2009 | Friedman et al. | ............. | 600/543 |
| 2009/0239711 A1 * | 9/2009 | Foley et al. | ...................... | 482/13 |
| 2009/0281442 A1 * | 11/2009 | Paz et al. | ......................... | 600/532 |
| 2010/0241026 A1 * | 9/2010 | Boukas | ........................... | 600/562 |
| 2011/0009762 A1 * | 1/2011 | Eichler et al. | .................. | 600/532 |
| 2011/0319783 A1 * | 12/2011 | Lindholt et al. | ............... | 600/529 |

OTHER PUBLICATIONS

International Preliminary Report on Patentability for International Application No. PCT/US2009/068961, dated Jun. 29, 2011.

Notification of Transmittal of the International Search Report and the Written Opinion of the International Searching Authority, or the Declaration for International Application No. PCT/US2011/061187, mailed Jun. 29, 2012.

Supplementary European Search Report, dated Jan. 9, 2014, received in connection with European Application No. 09835693.4.

* cited by examiner

FIG. 6

LUNG AEROSOL COLLECTION DEVICE

CROSS-REFERENCE TO RELATED APPLICATIONS

This application claims priority from U.S. Provisional Application No: 61/140,292 filed Dec. 23, 2008, the entire contents of which are incorporated herein by reference.

GOVERNMENT INTEREST

This invention was made at Georgia Institute of Technology and the Centers for Disease Control and Prevention. Therefore, the United States Government has certain rights in this invention.

FIELD OF THE INVENTION

The invention relates to sampling exhaled air. More specifically the invention relates to collection of materials such as pathogens from alveolar aerosols or other lower respiratory aerosols to the exclusion of significant contamination by upper respiratory materials such as solid and liquid pathogens contained therein.

BACKGROUND OF THE INVENTION

Pneumonia, or an inflammation of the lungs, is a leading cause of morbidity and mortality worldwide. In 2002, there were 451 million lower respiratory infections reported to the World Health Organization. Worldwide, pneumonia accounts for nearly 30% of all deaths in children under the age of five, killing more children than AIDS, malaria, and measles combined. In the United States, there were an estimated 1.4 million hospitalizations and 59,000 deaths due to pneumonia in 2002. Pneumonia can be caused by a variety of bacterial and viral pathogens, including *streptococcus pneumoniae, mycoplasma tuberculosis*, influenza viruses, respiratory syncytial virus, parainfluenza, adenovirus, rhinovirus, human bocavirus, influenza, *Mycoplasma pneumoniae*, hantavirus, and cytomegalovirus.

To treat this condition appropriately it is necessary to properly identify the pathogen in the lower airway. This can be done by checking for the presence of the pathogen, virus, bacteria or fungus, in the lung, i.e. alveoli and/or bronchioles. Obtaining a sample from the lung and confirming the etiology of pneumonia has proven difficult. For example, in the case of one of the leading causes of pneumonia, streptococcus pneumonia, as much as 70% of healthy people carry pneumococcus in their upper respiratory system. This makes it difficult with the usual method of specimen collection, a sputum specimen, to confidently determine if a positive detection for *S. Pneumoniae* indicates carriage or the cause of pneumonia. A sputum specimen is collected after passing through the upper respiratory tract and mouth and is, therefore, contaminated with upper respiratory tract organisms. More invasive techniques including bronchial lavage, laparoscopic alveolar biopsy, or pleural tap do indicate presence of an organism in the lung but carry greater risk to the patient and are costly and painful.

An easy to obtain sample of material from the diseased lung would greatly improve a physician's ability to diagnose and treat pneumonia. A sample of material from lung alveoli and bronchioles is also beneficial in various other situations such as determining the presence and concentration of alcohol in the blood stream and diagnosing disease processes such as lung cancer.

Accurate diagnosis of pneumonia is still a major problem and the field is innovating toward complex devices with multiple valves and chambers. There is an unmet need for a simple device for collecting a sufficient sample of lower airway material not contaminated by upper airway material for accurate detection clinical of pneumonia. Thus, there exists a need for a simple device and process for collection of lower respiratory air such as lung aerosols while minimizing or eliminating contaminating upper respiratory tract air from the sample. There further exists a need for a device that can collect materials such as pathogenic organisms from lower respiratory tract air without significant contamination from similar or identical organisms in the upper respiratory tract.

SUMMARY OF THE INVENTION

A lower respiratory aerosol sample collection device is provided that is simple, inexpensive, and accurate for the collection of aerosols from the alveoli and bronchioles of the lung while excluding contaminating material from the upper airway. The inventive device functions without the need for complex valving, switching, or actual collection of air from the lower respiratory system. The inventive device does not require: electronic detection, collection, or measuring devices; chamber(s); resistance elements or shapes; or particular positioning. The inventive collection device also allows a sample of lower airway material from multiple exhalations to be obtained without the need for significant resetting of the device or collection of the air from a prior breath.

An inventive device is optionally 50 percent or more effective at separating lower airway aerosols from upper airway material. More preferably, a device is 50-100 percent effective. Optionally, a device is 50, 60, 70, 80, or 90+ percent effective. Preferably, an inventive device is effective in a position with a shaft in a vertical orientation or 90 degrees either direction. Optionally, a shaft is in a lower position and the device will separate lower airway aerosols.

An inventive lung aerosol separation and collection device includes a conduit into which a patient or other subject exhales or coughs via a first open end. A conduit optionally includes a narrowed section or Venturi channel whereby the exhaled fluid passes. The breath travels through the conduit which is connected to a shaft that preferably has higher flow resistance than a second open end. The conduit is also fluidly connected to a chamber that serves to collect the upper airway air. As the upper airway air is expelled first during exhalation, the conduit fills to a predetermined volume. When full, the force of the full chamber allows the following lower airway air to be directed to the shaft and through the filter. It is preferred that the size of the chamber be less than 500 ml. The shaft is connected to a filter that lower airway air flows through. The filter functions to collect sample material from the lower airway air as it passes through. Target material such as bacteria, viruses, fungus, or other cellular or target materials are trapped in the filter while remaining lower airway air passes through the system.

An inventive device optionally includes a trap to collect liquid material that may contaminate the filter or does not represent the aerosolized target material of interest. A trap is preferably positioned at a region of the conduit that is substantially opposite the shaft.

An optional valve is present in the shaft or connected to the shaft whereby a force closes the valve prior to filling the chamber. The valve is preferably positioned in the shaft between the filter and the conduit. A valve is optionally a check valve, a quarter turn valve, diaphragm valve, globe valve, or other valve known in the art. Preferably, a valve is a check valve. Several types of check valves are operable illustratively including a ball, swing, clapper, stop, or a lift check valve. Most preferably, a check valve is a ball-check valve.

Optionally, a conduit includes a narrowed section or Venturi channel whereby the exhaled fluid passes. An inventive device preferably functions by creating a negative flow in the shaft during the initial phase of exhalation where upper airway air is first expelled. This negative pressure can passively force the valve into a closed position by fluid passing through the narrow region of the conduit.

A preferred conduit has a curvilinear upper surface continuous with a lower surface that extends between a first end and a second end of the conduit. It is preferred that the shaft be connected to the conduit in at the upper surface.

To direct proper positioning of the device in the oral cavity of a subject, one or more ridges are present on the conduit. Optionally, a first ridge is present in the upper surface and a second ridge is present in the lower surface. The ridges are optionally offset in distance from the first end. In one embodiment, a ridge is from 5-35 mm from the first end of the conduit. Preferably the ridge is greater than 10 mm from the first end of the conduit.

An inventive device also optionally includes a trap. A trap is preferably located on the lower surface. It is preferred that the lower surface at the trap is below the lower surface at the first end and the lower surface at the narrow region during operation. This forms a depression in the device that serves to trap unwanted liquids from passing into the narrow region.

A capacitive chamber is optionally present located between the filter and the conduit.

In addition to an open first end, an inventive device optionally includes a mouthpiece located at the first end. The mouthpiece optionally has a narrow cross sectional region and a wide cross sectional region and is connected to the first end at the wide region of the mouthpiece.

An inventive process of collecting a sample from lung aerosols is provided. The inventive process includes separating lung aerosols from upper airway air by passing the lung aerosols through a filter not exposed to upper airway air and collecting a sample from the filter. The inventive process also optionally includes collecting sample from a second breath of a subject by passing lung aerosols from the second breath through the filter. Optionally, lung aerosols from multiple breaths is passed through the filter. Optionally, an inventive process includes collecting or sampling upper airway air that is separated from lower lung aerosols.

A process of detecting or diagnosing a disease is also provided. A disease is optionally an infectious disease or a non-infectious disease illustratively cancer. The process includes separating lung aerosols from upper airway air and passing the lung aerosols through a filter not exposed to upper airway air. The process further includes collecting separated upper airway air and detecting the presence or absence of a pathogen in the lung aerosols and the upper airway air to diagnose the presence of a disease in the subject.

A process of detecting the presence or concentration of an analyte is also provided. The process includes separating lung aerosols from upper airway air and exposing the lung aerosols to a detector not exposed to upper airway air and detecting the presence or absence of an analyte in the lung aerosols. The process optionally further includes exposing upper airway air to a second detector and detecting the presence or absence of an analyte in the upper airway air.

DETAILED DESCRIPTION OF THE PREFERRED EMBODIMENTS

It is to be understood that the present invention is not limited to particular embodiments described, which may, of course, vary. It is also to be understood that the terminology used herein is for the purpose of describing particular embodiments only and is not intended to be limiting.

The invention has utility for the collection of lower respiratory tract air. The invention has further utility as a diagnostic aid for the detection and diagnosis of disease or abnormality. As the device is able to readily distinguish between the contents of the lower respiratory tract and the upper respiratory tract, the device is operable for detecting the presence of alcohol in the blood independent of recent consumption and contamination by residuary alcohol in the mouth or upper digestive tract.

The invention provides a segregated sampling of the aerosolized material from the lower airway through the combination of a single flexible chamber and separate sampling apparatus while minimizing the amount of contaminants from saliva and mucus collected from the oropharyngeal cavity. The device requires no power, active valves, or secondary apparatus.

The invention provides for the diagnosis of infectious pneumonia that is simple and inexpensive. The device segregates lower respiratory gas and aerosolized material from contaminants such as liquid from the mouth and gas or aerosolized pathogens from the oral cavity. Illustratively, a filter traps the lung pathogens without a complicating second chamber. The outflow tract through the filter provides for low resistance and variable breath volumes. A simple fluid dynamics Venturi pressure system maintains segregation of gases during exhalation. A shaped mouthpiece effectively prevents large amounts of oral liquids from entering the device. An air-liquid trap uses gas diversion to further reduce liquid contamination. An elastic chamber of variable volume is optionally adjusted to the lung volume of individual patients such as a child with reduced lung volume or an adult with higher lung volume. Pathogens detectable or collectable by the inventive device optionally include, but are not limited to, *Streptococcus Pneumonia*, *H. influenza*, *M. Tuberculosis*, viruses, and fungi. Analytes detectable or collectible by the inventive device illustratively include: cells such as normal cells or abnormal cells illustratively including cancer cells; proteins illustratively including amylase; nucleic acids such as DNA or RNA; cytokines; chemokines; nitrogen oxide(s); carbon dioxide; acetone; alcohol including ethanol; glucose, or other sugars; and surfactant. An analyte is optionally a blood analyte. A blood analyte is preferably a molecule that is present in the bloodstream of a subject and is detectable in lung fluid. Illustratively, the amount of alcohol and acetone, as two examples of an analyte, in a sample of lung aerosols will allow computation of total body fat as described in U.S. Pat. No. 4,114,422, the contents of which are incorporated herein by reference.

The inventive device has any number of clinical uses in interrogating the respiratory system. Pathogens causing pneumonia of the lower airway are preferably sampled using the device. Exhaled ethanol from the bloodstream is optionally sampled more accurately using the device than is achieved using prior art devices. Inspired samples of asbestos or coal are also optionally sampled to differentiate upper and lower airway origins. Cancer cells from the lower airway are differentiable from such cells present in upper airway origins. Oxygen in gas may need to be measured separately from oxygen in the liquid material in the upper airway.

As used herein the word "fluid" is defined as a non-solid substance. In a preferred embodiment a fluid is a gaseous substance. Illustratively a gas substance is air. Air is preferably air exhaled from a subject into the inventive device for separation and collection of material contained in the fluid. More preferably, air is coughed from a subject into the inventive device for separation and collection of lower airway aerosols.

As used herein the term "upper airway" air is defined as the air present in the oral cavity as the region external to the epiglottis. The volume of this air is dependent on the size of the subject. For a child the volume of upper airway air may be as little as 50 ml. For a large adult the volume may be as much as 300 ml. Typically, an average adult will expel upper airway air in the first 100 to 150 ml of exhaled breath.

As used herein the term "lower airway" air refers to air contained in the lungs, including bronchioles, alveolar sacs and alveoli when a subject has inhaled. The lower airway includes all anatomical structures internal to the epiglottis.

As used herein the term "alveolar air" is used synonymously with lower airway air and includes air present in the lungs prior to exhaling including that from the alveoli, bronchioles, and other lung passages.

As used herein the term "lung aerosols" means any material aerosolized in fluid from the lower airway.

It is appreciated that the inventive device operates without active or electronically controlled valves, colorimetric or other specific indicators, pistons, multiple collection or diversion chambers, condenser tubes, heating or cooling mechanisms. In a preferred embodiment an inventive device samples material in lung aerosols without collection of the air itself or sampling of the lung aerosols.

Figure 1:
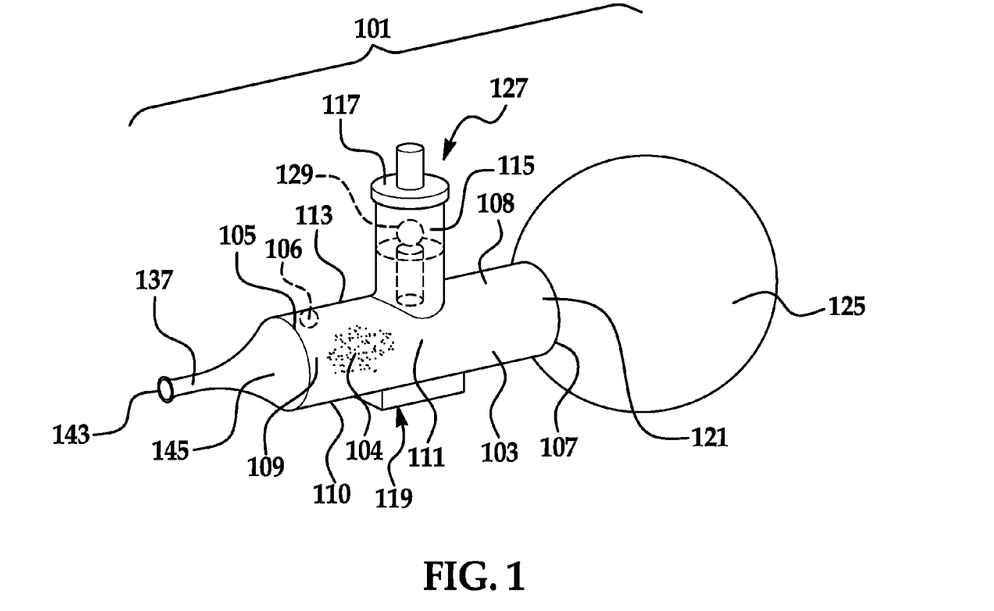
FIG. 1 represents a preferred embodiment of the device.

Referring to FIG. 1, an inventive device 101 includes a conduit 103 with a first end 105 and a second end 107. Fluid 104 passes through said conduit 103. The conduit is preferably used in a substantially horizontal orientation with respect to the elevation of the first end 105 and the second end 107. The conduit is optionally made from polymeric material, metal, glass, and the like.

In the pictured embodiment of FIG. 1, the conduit 103 is substantially linear so as to form a cylindrical cross sectional area. It is appreciated that the cross sectional area of the internal space of the conduit 103 need not be circular. The cross sectional area is optionally oblong, square, rectangular, triangular, irregular, or any other shape. The conduit 103 is optionally non-linear from the first end 105 to the second end 107. Preferably, the fluid path from the first end 105 through the device is not linear and has one or more bends so that particles with more density will impinge on the wall of the conduit lumen. The bend(s) causes particles with greater mass and momentum to hit the wall of the conduit 103, whereas lighter aerosolized particles will more easily pass therethrough. It is appreciated that relative sizing of the cross sectional areas of the ends 105, 107 to a narrowed internal region therebetween allows one to select the particle fraction such as an aerosol size for separation.

A conduit 103 has a curvilinear upper surface continuous with a curvilinear lower surface. The curvilinear shapes of the upper surface and lower surface are optionally correlated or identical or are optionally independent such that the internal dimensions of the conduit 103 are not constant between the first end 105 and the second end 107.

The conduit 103 is fluidly connected to a shaft 115. The shaft 115 preferably extends perpendicularly from the conduit 103. Optionally, the shaft 115 extends at an angle from the central axis of the conduit 103. The shaft 115 is preferably integral with the conduit 103. The shaft 115 is preferably made from the same material as the conduit 103 so as to form a single unified piece. The shaft 115 preferably bridges the conduit 103 to a sampling apparatus 117.

In one embodiment, the shaft 115 is spatially offset relative to a central axis of the conduit 103. FIG. 1 depicts an elevated offset in a preferred embodiment. This offset directs the denser liquid material away from the shaft 115 and into a trap 119 or other lower region of the conduit 103. The liquid material has a higher density and momentum than aerosolized particles and tends to travel in a straight line as fluid moves through the device 101. Thus, the conduit preferably is oriented in line with the first end 105 while the shaft 115 preferably extends at an angle from this line. Preferably, a shaft 115 is located on the upper surface 108 of the conduit 103.

The shaft 115 optionally incorporates a smaller opening or overlapping opening to further prevent liquids from entering as fluid passes through the device 101. A trap 119 is optionally located between the first end 105 and the shaft 115 on the conduit 103. The conduit 103 preferably forms a depressed shape with lower elevation with respect to the first end 105 and the shaft 115 so as to form a trap 119 so that liquid contaminant from the upper airway is segregated from the aerosolized pathogens or other material present in the fluid from the lower airway. This prevents the liquid contaminant from being transported to the distal ends of the device improving separation of alveolar material.

At the conduit second end 107 is preferably a chamber 125. Chamber 125 has an entrance opening that preferably provides lower flow resistance than the entrance opening of the first end 105 of the conduit 103. More preferably, the chamber entrance opening is of the same cross sectional area as the fourth area 121 of the conduit 103. The differences in flow resistance allows fluid flow to pass into the chamber 125 before the shaft 115 as flow will follow the path of least resistance. Fluid will then pass into the chamber 125 filling it. Preferably, the chamber 125 is made from a flexible material so that the chamber 125 will expand from the presence of incoming fluid to a maximum internal volume. The maximum internal volume is defined by the internal area of the chamber 125 and the elasticity of the chamber material. Preferably, the chamber is made from material with low elasticity. A chamber 125 is preferably elastic to provide shock-absorbing compliance during coughing. Optionally, the chamber 125 is made from material with substantially no elasticity. The chamber is optionally made from natural or synthetic materials illustratively including latex, rubber, polymeric material, glass, metal, and the like.

In an embodiment with a flexible chamber 125, the volume of chamber 125 will increase to a predetermined amount with breath from the upper airway. After inflation of chamber 125, resistance to further inflation occurs proving sufficient resistance such that additional exhaled breath from the lower airway will then pass into the shaft 115. In one embodiment, the aerosol content is filtered for pathogen directly. In another embodiment, the entire lower airway breath is collected in a second chamber.

Figure 2A:
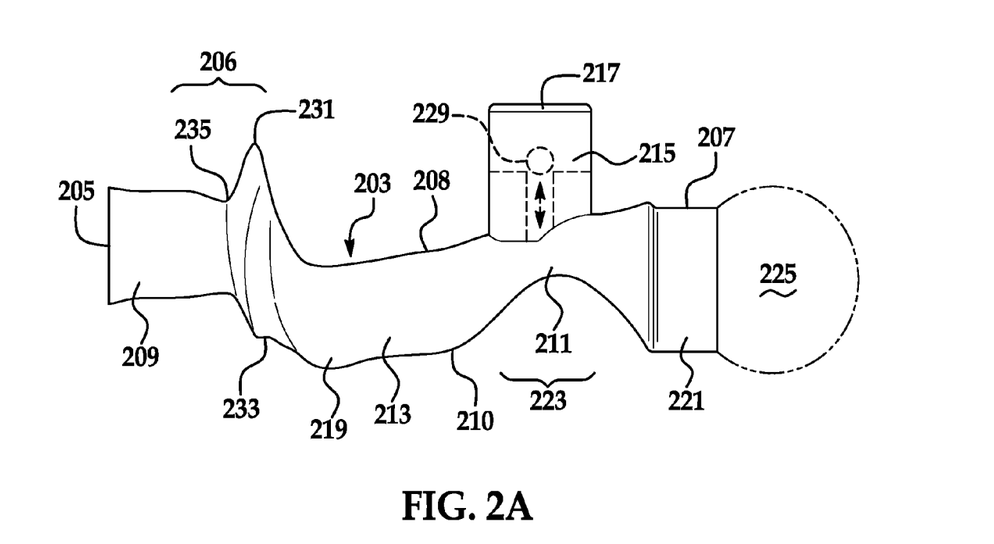
FIG. 2 represents two perspectives on the inventive conduit and shaft of a preferred embodiment of the inventive device.
Figure 2B:
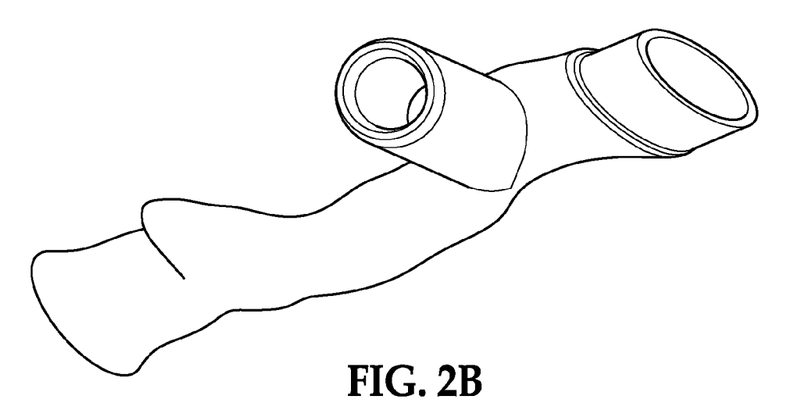

The chamber 125 is preferably a flexible material that can be collapsed by physical force or expanded by capture of upper respiratory air. Optionally, a chamber 125 is a solid material such as glass, metal, rigid polymers and the like.

The average normal (tidal) exhalation in a healthy adult is approximately 500 ml. Of this 500 ml, the initial 150 ml of exhaled gas is from the upper airway including the trachea, and oropharyngeal space. This portion of gas is commonly referred to as the "dead space" since it does not contribute to oxygen refreshment to the lungs. The latter 350+ ml of exhaled gas comes from the lower respiratory airway and alveoli. Thus, chamber 125 preferably expands to 150 ml and then provides resistance to further inflation. The lower airway breath of 350 ml is then diverted into the shaft 115. By separating the initial 150 ml from the 500 ml sample, it is possible to isolate the contaminating bacteria in the first 150 ml from the true pneumonia pathogens present the alveolar space contained in the subsequently exhaled 350 ml of air.

A chamber 125 is preferably of sufficient internal volume to capture all upper respiratory air. Preferably, a chamber 125 has an internal volume of less than 300 ml. Optionally, a chamber has a volume between 25 ml and 300 ml. More preferably, a chamber has an internal volume between 50 and 150 ml. Most preferably, a chamber has an internal volume of 100-150 ml.

The chamber 125 is optionally adjusted or replaced with a different size chamber to collect different volumes depending on the size of the patient. For instance, a child may require the chamber to collect a volume of only 50 ml, while a large adult may require collection of 300 ml.

A shaft 115 preferably terminates in or includes a sampling apparatus 117. A sampling apparatus 117 is optionally a detector or a filter. In a preferred embodiment a sampling apparatus 117 is a filter. A filter is preferably of any suitable material to allow gaseous fluid to pass through the filter while trapping materials contained in the fluid such as pathogens including virus particles, bacteria, yeast, fungus, and the like. A filter optionally traps environmental contaminants such as asbestos, fiberglass, pesticides and the like. A filter is optionally made from paper, gelatin, polymers, glass, or other material. The material is preferably operable for collecting target material. Optionally, a filter is sized so as to collect some targeted materials while letting others pass thorough. Illustratively, a filter is used to trap bacteria. Optionally, bacteria is *S. pneumonia*. Optionally, a filter will trap virus particles. Optionally, a filter is made of reactive material that will interact with a target molecule or pathogen thereby trapping the molecule or pathogen in the filter while selectively allowing non-targets to pass through the filter. In one embodiment a filter is less than 100% effective at trapping a target. Filter materials suitable for use with the inventive device are known in the art and are obtained from sources known in the art, illustratively, 3M Corp. (St. Paul, Minn.). In a preferred embodiment the VBMax filters from A-M Systems, Inc. (Carlsborg, Wash.) are used.

A filter will preferably allow the velocity and volume of lower airway fluid associated with a cough to readily pass though the filter without significant resistance so material from the coughed lower airway fluid can be readily collected on the filter. Without significant resistance is preferably no more resistance than necessary to trap desired material on or in the filter. It is preferred that the device provide minimal resistance to lower airway fluid passing through the shaft to contact a detection apparatus.

Fluid is optionally exhaled fluid from a subject, fluid exhaled during a cough, or a rapid forced exhalation.

In one embodiment a filter is present in a cartridge that attaches to a shaft 115. Optionally, the filter cartridge 127 attaches to a shaft 115 by way of a press fit. Optionally, a filter cartridge 127 attaches to a shaft 115 by a screw fit, clamp, intermediate connector, or other type of fitting known in the art.

An inventive device optionally includes a valve 129 between the sampling apparatus 117 and the conduit 103. A valve 129 is preferably housed within a shaft 115. It is appreciated that a valve is optionally placed between the shaft 115 and the conduit 103, or between the shaft 115 and the sampling apparatus 117, or filter cartridge 127. A valve preferably will close the internal area of the shaft 115 reducing or eliminating fluid flow from the conduit 103 to the shaft 115. A valve is optionally a check valve, a ball valve, a diaphragm valve, a globe valve, and the like. Preferably, a valve is a check valve. Types of check valves illustratively include a ball, diaphragm, swing, clapper, stop-check, lift-check, and the like. In a preferred embodiment a valve is a ball-check valve. A valve is preferably a passive valve such that user input other than exhaling or coughing is not required for proper operation of the device.

An inventive device optionally includes a mouthpiece 137 located at the first end 105. A mouthpiece 137 is optionally a tapered shape whereby the taper is preferably not constant. The tapered shape produces a narrow region 143 and a wide region 145. The mouthpiece 137 preferably extends posterior to the teeth of a subject during exhalation. This extension prevents saliva and other mouth contents from entering the device. The extension also reduces the amount of upper airway material entering the collection device. Preferably, the mouthpiece 137 has an opening entrance at the proximal end which is located posterior to the teeth of a subject during exhalation. More preferably, the entrance is more than 10 mm posterior to the teeth. The mouthpiece optionally a round, oval, square, or rectangular opening. In a preferred embodiment the proximal opening of the mouthpiece is smaller in cross sectional area than the exit to the conduit 103. This mouthpiece configuration prevents unwanted upper airway and oral cavity material from entering the collection device during use. By positioning the entrance of the device appropriately, the liquid saliva and sputum does not enter the device in large amounts. Mouthpieces of different size entrance openings are optionally utilized for patients of different size for collecting coughs versus deep breath exhalation. A one-way valve is optionally included in the mouthpiece 137 to prevent backflow.

Referring to FIG. 2 maintaining like numerals, a shaft 215 is preferably located at the narrowed region ("Venturi channel") 223 of the conduit 203. Without being limited to one operational mechanism, the increased fluid flow rate through the Venturi channel 223 causes a negative pressure within the shaft 215. The negative pressure brings the valve 229 into a closed position, thus, preventing fluid from entering the shaft prior to full inflation of the chamber 225. It is appreciated that this negative pressure is present independent of the presence of a valve in the shaft such that fluid is prevented from entering the shaft prior to chamber inflation simply due to the increased fluid flow rate in the Venturi channel 223 of the conduit 203. As such, the valve is optional, yet preferred.

An inventive conduit optionally has a first cross sectional area 209 defined as the internal cross sectional area at the first end 205. A cross sectional second area 211 is the internal cross sectional area at a point some distance toward the second end 207. Preferably, the first cross sectional area 209 is larger than the second cross sectional area 211. Optionally, the first cross sectional area 209 is the same as the second cross sectional area 211. It is appreciated that a first cross sectional area 209 is optionally smaller than a second cross sectional area 211. A third cross sectional area 213 is defined as an internal cross sectional area at a location in the conduit 203 intermediate of the first cross sectional area 209 and the second cross sectional area 211.

A preferred embodiment includes a conduit with a fourth area 221. Preferably, the second area 211 is smaller than the third area 213 and the fourth area 221. This forces the fluid into an area of lower cross sectional area forming a Venturi channel 223. The Venturi channel is a narrowed flow section that causes higher fluid velocity and consequently, lower dynamic pressure through the flow section. This creates a negative pressure in the shaft 215 during movement of upper airway fluid through the conduit 203. The Venturi channel 223 will prevent fluid motion toward the filter 217 during the first part of exhalation when upper airway fluid is passing thorough the device.

A conduit 203 preferably includes one or more positions 206 defining a distance from the teeth of a subject to the first end of the device when the device is used in the mouth of a subject. A position 206 is optionally an identifiable region on the conduit that a user or administrator locates to associate the teeth of a user for proper positioning of the device. A position 206 is optionally greater than 10 millimeters from the first end. Optionally, a position 206 is 10 to 80 millimeters from the first end. In a most preferred embodiment, a position 206 is from 20 to 30 millimeters from the first end. A position 206 is optionally one or more locations such as a line, color change, ridge, channel, depression, joint, or other visual, tactile, auditory, or measurably identifiable location.

In a preferred embodiment a position is defined by one or more ridges. A ridge is preferably dimensioned so that a subject's teeth will engage the ridge during exhalation. A first ridge 231 is preferably located on the upper surface 208 of the conduit 203. A second ridge 233 is located on the lower surface 210 of the conduit 203. The ridges optionally define a region of increased outer circumference. Located toward the first end 205 on the conduit 203 is optionally a channel 235 that acts as a position. During operation a user fits his teeth within the channel at the point of the ridges. This helps define the location of the device in the oral cavity. Preferably, the ridges 231, 233 are between 5 and 80 mm from the first end 205. More preferably, the ridges 231,233 are greater than 10 mm from the first end 205. Most preferably, the ridges 231, 233 are 25 mm from the first end 205. Optionally, the first ridge 231 is positioned further from the first end 205 than the second ridge 233. This offset orientation comfortably accommodates a natural overbite of a user. Optionally, a first ridge 231 is positioned nearer to the first end 205 than the second ridge 233.

A trap 219 is positioned between the narrow region 223 and the ridges 231, 233. This trap 219 defines a region in the lower surface 210 of the conduit 203 below the lower surface at the first end 205 and below the lower surface at the narrow region 223. This configuration collects unwanted liquid as the fluid passes from the first end toward the narrow region due to the curvilinear shape of the conduit 203.

Figure 3:
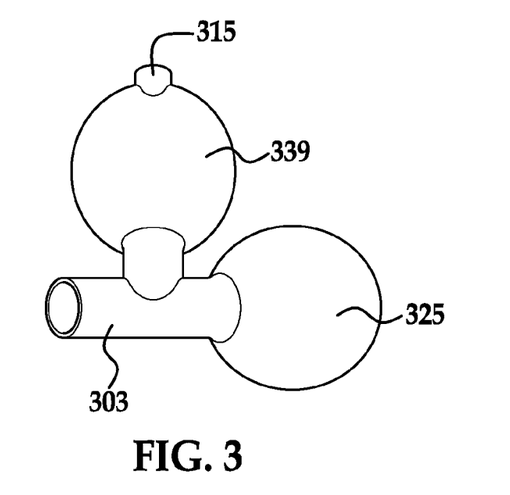
FIG. 3 represents an alternative embodiment of the inventive device.

Referring to FIG. 3, an inventive collection device optionally includes a second chamber such as a capacitive chamber 339 located between the conduit 303 and the shaft 315. A capacitive chamber 339 operates to absorb the high pressure/volume of a cough that can be slowly bled out to the chamber 325 without allowing upper airway air to enter the filter. A capacitive chamber 339 is optionally an enlargement of the shaft 315 or is a pliable section that will expand in the presence of a rapid increase in pressure/volume due to a cough. The patient may be asked to inhale deeply and cough to expel more contents from the alveoli. The device can accommodate high pressures generated by such a cough and still segregate the lower airway material.

Figure 4:
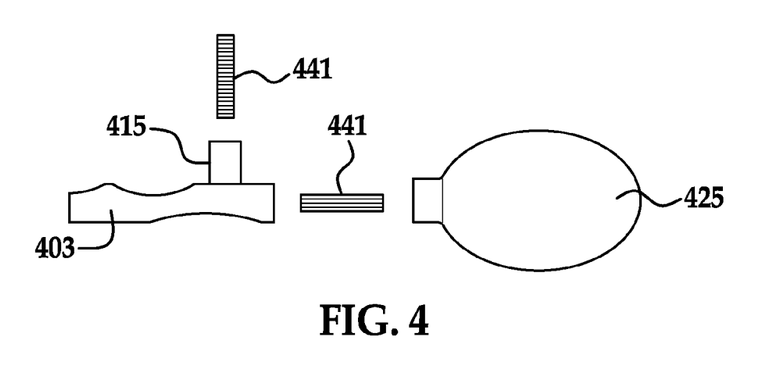
FIG. 4 represents a schematic of an analyte detection embodiment of the inventive device.

As illustrated in FIG. 4, in one embodiment a sampling apparatus is one or more detectors 441. A detector 441 is optionally positioned in a shaft 415 so that lower airway/lung aerosols is exposed to a detector during an exhalation of a subject. Optionally, a second detector is present within the conduit 403. The second detector is preferably located distally from the shaft within the conduit 403 or within the chamber 425 so that it is not exposed to lower airway air and is used to detect the presence of a target in the upper airway. A detector is optionally operable to detect the presence or absence of a bacteria, virus, fungus, antibody, protein, or chemical such as carbon dioxide, carbon monoxide, nitric oxide, alcohol and the like. In one embodiment a detector is capable of detecting the presence of alcohol in the lower or upper airway of a subject. A detector is optionally a surface, a labyrinth, a trap, sticky substance, warmed or cold surface, metal, or electrical, chemical or mechanical sensor. A sensor or other detector is illustratively operable to detect a molecule or pathogen, either by color, optical, or electronic or other chemical means.

One or more parts of an inventive device are optionally reusable. Illustratively, a conduit is sterilizable such as by autoclaving for reuse to reduce possibility of contamination from a prior use. Optionally, the conduit and shaft are reusable. Optionally, the entire device is reusable.

While the inventive device is preferably used with the first end positioned posterior to the front teeth, it is appreciated that the device is similarly functional positioned near, at, or in front of the teeth.

A process is provided for detecting the presence or absence of material from the lower airway as exhaled, preferably by coughing, by a subject to the exclusion of material from the upper airway. An inventive process illustratively includes separating lung aerosols from upper airway air using an inventive device; contacting the lung aerosols with one or more sampling apparatuses, optionally excluding upper airway air from contacting a sampling apparatus, and optionally collecting a sample on the sampling apparatus.

An inventive process optionally includes separating lung aerosols from a second breath. A breath as used herein is a single round of respiration including inhaling and exhaling. Exhaling preferably includes one or more coughs. Collecting material from a cough or multiple coughs is most preferred. The inventive device is operable for separating lung aerosols from as many breaths as is desired to improve detection of target material. As the exit of the shaft preferably freely dispels air, as much air as is desired is optionally passed through the filter by way of collection of several successive exhalations. The device preferably does not require collection of the lower airway air for reuse or sampling. The inventive process preferably collects aerosols from two exhaled breaths. Optionally, the inventive process includes collection of multiple breaths. Multiple breaths is optionally two, three, four, five, six, seven, eight, nine, ten, or more breaths. It is appreciated that the device is not limited to any number of breaths.

An inventive process optionally includes collecting the upper airway fluid. Upper airway aerosols or liquid are optionally collected by removing the material trapped in the chamber or in the conduit following an exhaled breath. A chamber optionally has a valve or other collection opening to facilitate collection of upper airway material. The upper airway aerosol is optionally sampled. A second filter, detector, or sensor is optionally present within or at an exit portion of a chamber, in the conduit, or in the chamber for collection of the aerosols. A one-way valve is optionally present in the conduit preferably positioned toward the second end such that upper airway air may freely flow into the chamber until maximal expansion. After the exhalation is complete a user optionally collapses a chamber optionally forcing collected upper airway air through a second sampling apparatus capturing, sensing, or detecting upper airway material without forcing this material back into the conduit preventing possible contamination of the filter in the shaft.

Detection of material from either the upper airway or the lower airway is optionally by polymerase chain reaction (PCR), real-time PCR, reverse-transcription PCR, enzyme linked immunosorbant assay (ELISA), mass spectrometry, liquid chromatography, Southern blotting, western blotting, northern blotting, enzymatic assay, culturing, cell infection, other assays known in the art, or combinations thereof to selectively amplify or identify material from either lower airway aerosols or upper airway liquid or aerosols. The aforementioned detection or identification methods are generally known to those of skill in the art and are described in detail in methodology treatises such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992; among others. The contents of each of which are incorporated herein by reference.

A process of diagnosing a disease is presented including separating lung aerosols from upper airway aerosols by passing the lung aerosols through a filter and excluding upper airway aerosols; collecting the upper airway material; and detecting the presence or absence of a pathogen, disease cell, protein, or other target in the lung aerosols or upper airway. A disease is optionally diagnosed by detecting a target. Illustratively, a disease is cancer. A user optionally diagnoses the presence of cancer cells by location to either the lower airway or the upper airway.

A process for detecting an analyte in the blood stream of a subject is provided. The inventive process includes separating lung aerosols from upper airway aerosols by a subject exhaling; and detecting the presence or absence of an analyte on a filter or detector present in lower airway aerosols.

Various aspects of the present invention are illustrated by the following non-limiting examples. The examples are for illustrative purposes and are not a limitation on any practice of the present invention. It will be understood that variations and modifications can be made without departing from the spirit and scope of the invention.

Example 1

Figure 5:
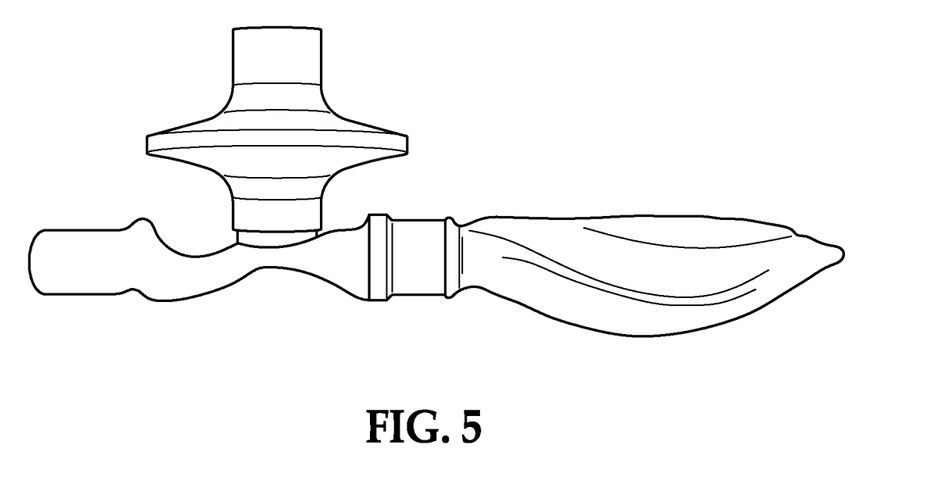
FIG. 5 represents a preferred embodiment of an inventive device.

A breath separation and collection device is depicted in FIG. 5. The device includes a single piece conduit and shaft substantially as depicted in FIG. 2. A ball-check valve is present in the shaft. A filter is connected to the shaft and housed in a filter cartridge. A flexible chamber is attached to the second end of the conduit.

Human subjects (patients) are sampled as approved by Georgia Institute of Technology Institution Review Board as IRB Protocol H08353. Patients are asked to expel a deep cough into the device and continue exhaling residual air in the lungs. Coughing and sneezing aerosolize a greater number of lower lung pathogens as compared to exhalation alone.

Example 2

Oxygen Separation Test: Oxygen absorption by blood occurs only in the lower airway (alveoli), and not in the upper airway (mouth, trachea). Thus the oxygen level in the lower airway is expected to be less than that of the upper airway. Ambient atmosphere contains approximately 21% oxygen, while expired air is about 16.5% oxygen. The oxygen content from the upper airway chamber is tested and compared with a sample from a collection chamber located on a shaft. The percentage of oxygen in each sample is measured with an oxygen meter (Teledyne Analytical Instruments, Model # GB 300). The experiment is repeated using the device of Example 1 ten times with statistical significance defined at the $p<0.05$ level.

Figure 6:
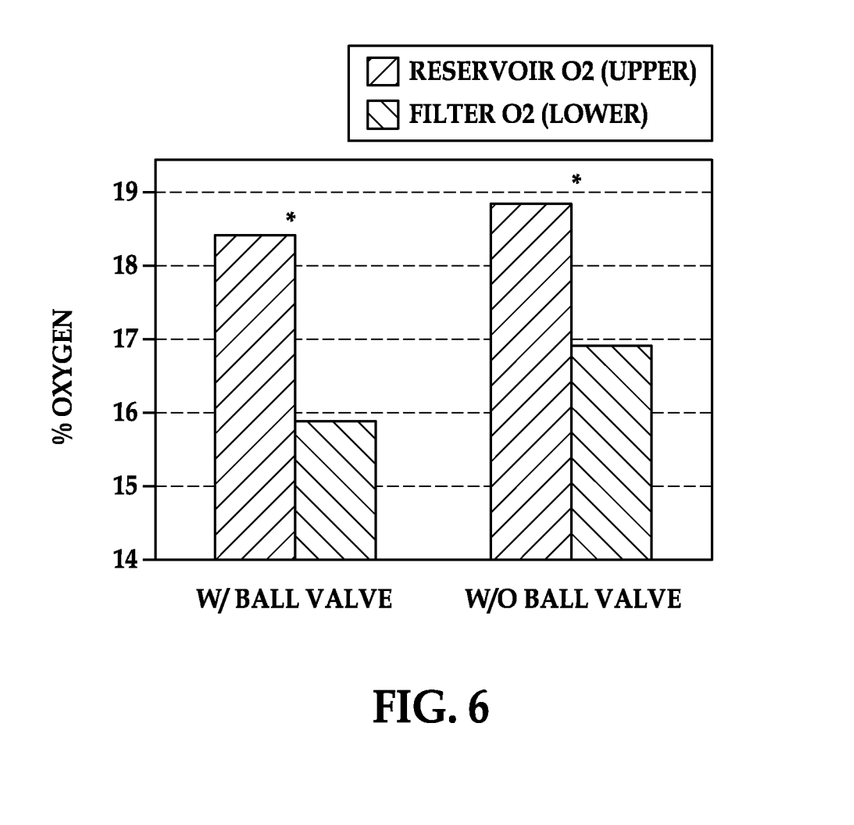
FIG. 6 represents the oxygen levels in upper airway air or lower airway air as obtained by the inventive device.

As depicted in FIG. 6, the average percentage of oxygen in lower airway sample as passed through the filter is 15.9%, whereas the average upper airway sample is 18.4%. The average percentage of the room air oxygen as breathed by the patients is 20.9%. The lower airway sample is statistically lower than the upper airway sample or the room air with a p-value of $<0.0001$, $n=10$. These data indicate that the inventive device successfully separates lower airway air from upper airway air.

A second test variation is performed to assess the function of the ball valve. The Oxygen Separation Test is performed without the ball valve to determine the effect of the ball valve on the separation of lower airway samples from upper airway oxygen content. In the absence of the ball portion of the ball-check valve, the average percentage of oxygen in the lower airway sample is 16.9% compared to the upper airway sample of 18.9% ($p<0.0001$). The average percentage of oxygen in the lower airway sample with the ball valve is 15.9% and without the ball valve is 16.9% ($p<0.0001$).

Example 3

Detection of blood ethanol in lower-respiratory air. Ingested ethanol appears 20 minutes later in the blood stream and becomes volatile in the alveolar space, not in the upper airway. Two 0.02% breath alcohol testers (Advanced Safety Devices) are connected to the inventive device. One detector samples lower airway air and is connected to the shaft. The second detector is positioned within the chamber. Participants drink 50 proof alcohol, 60 ml for females and 80 ml for males. Participants then rinse the mouth with water but are not allowed to swallow the water. After 20 minutes, the participant drinks an 8 oz glass of water and then deep coughs and exhales residual air into the inventive device as described in Example 1. The color changing crystals are allowed to develop for 2 minutes. The paired breath alcohol testers are photographed and resulting color analyzed with photo editing software and the quantitative saturation and blue levels are measured.

As a control, the volume of lower airway aerosols is directed into the chamber and thus, through the second detector. The participant coughs and exhales residual air into the device. After 2 minutes, the breath alcohol tester with restricted volume is photographed and analyzed.

In all cases, the lower airway samples change color, whereas the upper airway samples do not. The differences results in p-values as follows: saturation—p=0.0015; and blue—p=0.0019. As a control, the chamber volume is separately tested to assure that this volume was enough to convert the colorimetric crystals. Since these three values of the alcohol crystals are significantly different the device successfully samples the volatiles generated in the lower airway separately from the upper airway.

Example 4

Negative pressure created by a Venturi channel: The filter of the device of Example 1 is replaced with a thin plastic bag filled with 50 ml of air and the chamber is removed. The direction of flow through the Venturi is quantified by the time required to deflate a fixed 50 ml thin bag. With every exhalation, the 50 ml bag attached to the filter tube fully deflated over an average of 1.25+/−0.25 s. Table 1 shows the results of the Venturi test illustrating deflation of the filter bag. Thus, the Venturi creates a negative pressure in the shaft. The results demonstrate that the device prevents the initial upper airway gas from passing through the collection chamber during deep coughing.

TABLE 1

| n | Time (s)* |
|---|---|
| 1 | 1.47 |
| 2 | 0.93 |
| 3 | 1.6 |
| 4 | 1.07 |
| 5 | 1.2 |
| AVERAGE: | 1.25 +/− 0.25 |

*Time to deflate bag over filter while blowing through device.

Example 5

Proper positioning of the device in the mouth: The device of Example 1 is tested in the correct position with the teeth in the channel at the base of the ridge and the first end extending 25 mm proximal to the teeth for the correct position and compared with an incorrect position with the opening at the first end of the device less than 10 mm proximal to the teeth. After deep coughing into the device, the amount of liquid that enters the device is measured and recorded for an initial oral volume of volume of 5, 7.5, 10, and 15 ml of water. The experiment is repeated for a total of three measurements for each initial volume of water.

When the mouthpiece is correctly positioned, no water enters the device, even when the amount of water starting in the mouth is increased to 15 ml (Table 2). A significant amount of water enters the device with incorrect device positioning.

TABLE 2

| | Ending Volume in device (ml)‡ | | |
|---|---|---|---|
| Initial Oral Volume (ml)† | Correctly Positioned Mouthpiece | Incorrectly Positioned Mouthpiece | p-value |
| 5 | 0 | 0.8 | 0.0075* |
| 7.5 | 0 | 3.7 | 0.0142* |
| 10 | 0 | 5.5 | 0.0062* |
| 15 | 0 | 7.5 | 0.0020* |

*Statistically significant
†Volume of liquid expelled into device

The inventive device functions with dramatic angle of positioning relative to the plane of the face. When the device is placed 45 degrees from the perpendicular to the plane of the face in any direction no liquid enters the device, as long as the mouthpiece is positioned correctly with the lips at the ridge on the mouthpiece and the opening behind the teeth.

Example 6

Phlegm Exclusion Test: A 2.5 ml volume of viscous solid jelly is used as a surrogate for phlegm in the oral cavity. The participant coughs into the device with proper and improper mouthpiece placement. The amount of jelly on the filter of the device of Example 1 is measured and recorded. This amount is compared to the control of expectorating the jelly sample directly into a sputum cup. When the device is correctly positioned no phlegm attaches to the device filter. In the one trial where jelly was observed on the filter the amount was less than 1% the starting volume.

Example 7

Collection of liquid in the trap: The device of Example 1 is tested whereby the volume of material contained in the trap during deep coughing is measured after successively larger oral volumes of 1, 2, 3, and 4 ml of water is present in the mouth prior to cough. The experiment is repeated three times. With a starting oral volume of 1 ml of liquid, 0.5 ml of liquid is dispose in the liquid trap after the deep cough. The results of the Trap Test are shown in Table 4. The liquid trap effectively captures 0.5 to 0.8 ml of oral liquids from reaching the outlets of the device during deep coughing.

TABLE 4

| Oral Volume (ml) | Volume Collected in Trap (ml) |
|---|---|
| 1.0 | 0.5 |
| 2.0 | 0.6 |
| 3.0 | 0.6 |
| 4.0 | 0.8 |

Example 8

The device of Example 1 is used with a VBMax filter. A Bacterial Filtration Efficiency Test and a Viral Filtration Efficiency Test are performed. Both test procedures are adapted from ASTM F2101. The bacterial filtration efficiency test uses the challenge organism *Staphylococcus aureus* (procedure number STP0009 Rev 02). The viral filtration efficiency test uses bacteriophage φX174 as the challenge organism.

The average Bacteria Filtration Efficiency is found to be 99.99977%. For the Viral Filtration Efficiency, the average filtration efficiency is 99.9975% with a mean particle size of 2.8 μm.

Various modifications of the present invention, in addition to those shown and described herein, will be apparent to those skilled in the art of the above description. Such modifications are also intended to fall within the scope of the appended claims.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A process of sampling aerosolized lung material comprising: providing a collection device comprising a conduit having a first open end and a second end, said conduit connected to a filter; separating upper airway fluid from aerosolized lung material lower airway fluid by inserting said first open end of said collection device a distance posterior to at least one tooth of a subject, wherein the first open end is located in the oral cavity of the subject, and sampling the aerosolized lung material by passing the aerosolized lung material through said conduit, while the first open end is located in the oral cavity of the subject, said aerosolized lung material lower airway fluid traversing said filter to trap aerosolized material in said filter.

2. The process of claim 1 wherein said distance is 5 millimeters or more posterior to at least one tooth of the subject.

3. The process of claim 1 wherein said distance is between 5 and 80 millimeters posterior to at least one tooth of the subject.

4. The process of claim 1 wherein said distance is from 20 to 30 millimeters posterior to at least one tooth of the subject.

5. The process of claim 1 wherein said device further comprises an identifiable position on said conduit between said first open end and said second end, said position defining said distance during collection of aerosolized material from a lung.

6. The process of claim 1 wherein said device further comprises a shaft fluidly connected to said conduit; at least a portion of said shaft between said conduit and said filter.

7. The process of claim 1 wherein said device further comprises a chamber fluidly connected to said conduit at said second end.

8. A process of discriminatorily sampling lower airway material comprising: providing a collection device comprising a conduit having a first open end and a second end, said conduit connected to a sampling apparatus; separating upper airway fluid from lower airway aerosolized material by inserting said first open end of said collection device a distance posterior to at least one tooth of a subject, wherein the first open end is located in the oral cavity of the subject; and contacting said lower airway aerosolized material with said sampling apparatus to sample the aerosolized lung material by passing the aerosolized lung material through said conduit, while the first open end is located in the oral cavity of the subject.

9. The process of claim 8 wherein said sampling apparatus is a filter or a detector.

10. The process of claim 8 wherein said distance is greater than 5 millimeters posterior to at least one tooth of the subject.

11. The process of claim 8 wherein said distance is between 5 and 80 millimeters posterior to at least one tooth of the subject.

12. The process of claim 8 wherein said distance is between 20 and 30 millimeters posterior to at least one tooth of the subject.

13. The process of claim 8 wherein said material is an analyte.

14. The process of claim 13 further comprising:
detecting the presence or absence of said analyte interacting with said sampling apparatus.

* * * * *